(12) United States Patent
Shippen

(10) Patent No.: US 10,357,220 B2
(45) Date of Patent: Jul. 23, 2019

(54) DATA TRANSFER ACROSS A ROTATING BOUNDARY

(71) Applicant: Analogic Corporation, Peabody, MA (US)

(72) Inventor: Peter Daniel Shippen, Ipswich, MA (US)

(73) Assignee: Analogic Corporation, Peabody, MA (US)

( * ) Notice: Subject to any disclaimer, the term of this patent is extended or adjusted under 35 U.S.C. 154(b) by 252 days.

(21) Appl. No.: 15/519,585

(22) PCT Filed: Oct. 16, 2014

(86) PCT No.: PCT/US2014/060834
§ 371 (c)(1),
(2) Date: Apr. 17, 2017

(87) PCT Pub. No.: WO2016/060666
PCT Pub. Date: Apr. 21, 2016

(65) Prior Publication Data
US 2017/0251994 A1 Sep. 7, 2017

(51) Int. Cl.
*A61B 6/03* (2006.01)
*H04W 4/80* (2018.01)
(Continued)

(52) U.S. Cl.
CPC .......... *A61B 6/56* (2013.01); *A61B 6/032* (2013.01); *G01N 23/046* (2013.01); *H01F 38/18* (2013.01);
(Continued)

(58) Field of Classification Search
CPC .... A61B 6/032; A61B 6/56; G01N 2223/304; G01N 2223/401; G01N 2223/643; G01N 23/046; H01F 38/18; H04W 4/80
See application file for complete search history.

(56) References Cited

U.S. PATENT DOCUMENTS 6,914,957 B2   7/2005   Dafni et al.
7,079,619 B2   7/2006   Katcha et al.
(Continued)

FOREIGN PATENT DOCUMENTS

EP   0510926 A2   10/1992
EP   2688078 A1   1/2014

OTHER PUBLICATIONS

International Search Report related application No. PCT/US14/60834 dated Jul. 14, 2015, pp. 12.

*Primary Examiner* — Mark R Gaworecki
(74) *Attorney, Agent, or Firm* — TraskBritt

(57) ABSTRACT

Among other things, a data communication system wirelessly transmits data between a stator and a movable unit (e.g., a rotor) as part of a computed tomography (CT) imaging modality. The data communication system includes a first magnetic portion including a first magnetic material. The first magnetic portion extends along a first axis. The data communication system includes a first conductive portion including an electrically conductive material. The first conductive portion is at least partially surrounded by the first magnetic portion. The first conductive portion extends along a second axis that is substantially parallel to the first axis. The first conductive portion will at least one of generate an electromagnetic field corresponding to data to be transmitted, or have induced therein a current based upon a received electromagnetic field, where the current is a function of the data to be transmitted.

20 Claims, 7 Drawing Sheets

(51) Int. Cl.
   *H01F 38/18*   (2006.01)
   *A61B 6/00*    (2006.01)
   *G01N 23/046*  (2018.01)

(52) U.S. Cl.
   CPC ........ *H04W 4/80* (2018.02); *G01N 2223/304* (2013.01); *G01N 2223/401* (2013.01); *G01N 2223/643* (2013.01)

(56) References Cited

U.S. PATENT DOCUMENTS

| | | |
|---|---|---|
| 7,502,438 B2 | 3/2009 | Nakagawa et al. |
| 7,634,046 B2 | 12/2009 | Krumme |
| 2013/0127580 A1 | 5/2013 | Dobbs |
| 2013/0259202 A1* | 10/2013 | Sloutsky .............. H04B 5/0093 378/98 |
| 2013/0279647 A1 | 10/2013 | Krupica et al. |
| 2014/0085042 A1 | 3/2014 | Dobbs |

* cited by examiner

DATA TRANSFER ACROSS A ROTATING BOUNDARY

CROSS-REFERENCE TO RELATED APPLICATIONS

This application is a national phase entry under 35 U.S.C. § 371 of International Patent Application PCT/US2014/060834, filed Oct. 16, 2014, designating the United States of America and published in English as International Patent Publication WO 2016/060666 A1 on Apr. 21, 2016.

BACKGROUND

The present application relates to the transference of information over an airgap separating two members configured for relative rotation. It finds particular application in the context of computed tomography (CT) imaging applications, where at least one of a first data communication component or a second data communication component is located on a rotor and an airgap separating the first data communication component from the second data communication component is small (e.g., 20 mm or less). However, it may also apply to other applications, such as explosive detection machines, radar antennas, etc. where communication signals are wirelessly transferred.

Today, CT and other radiation imaging modalities (e.g., single-photon emission computed tomography (SPECT), mammography, projection radiography, etc.) are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Some radiation imaging modalities, such as CT, are configured to generate volumetric data corresponding to an object under examination. To generate this volumetric data, the CT imaging modality is typically configured to rotate a radiation source and a detector array about the object under examination (e.g., causing the object to be viewed from a plurality of angles). For example, the radiation source and/or the detector array may be mounted to a rotor, also referred to as a rotating gantry, configured for rotation relative to a stator, also referred to as a stationary unit.

Given that the radiation source and the detector array are mounted on the rotor, power and control information (e.g., instructing the radiation source and/or other electronic components how to operate) are typically supplied to the rotor from the stator. Moreover, imaging data (e.g., data generated in response to the detection of radiation by the detector array) and/or status information (e.g., indicative of a status of various components mounted to the rotor) are typically transferred from the rotor to the stator. It may be appreciated that the volume of data transferred, particularly with respect imaging data, may be quite large. For example, some imaging modalities may require transfer speeds of up to 5 gigabits per second (e.g., particularly if the rotor does not comprise a storage medium to temporarily store data until the data can be transferred).

Conventionally, slip-ring assemblies have been used to transfer power and/or information (e.g., control information, status information, and/or imaging data) between the stator and the rotor or more generally between a movable unit and a stator (or between two movable units) through the physical contact of two materials (e.g., via a sliding contact). For example, a slip-ring attached to the stator may comprise metal brushes that are configured to physically contact electrically conductive surfaces (e.g., metal brushes) comprised on a slip-ring attached to the movable unit, allowing power and/or information to be transferred between the stator and the movable unit.

While the use of slip-ring assemblies has proven effective for transferring power and/or information between a stator and a movable unit (e.g., such as a rotor) and/or between two movable units, conventional slip-ring assemblies may generate dust or particles (e.g., as metal brushes wear), may be unreliable (e.g., again as contact surfaces, such as metal brushes, wear), and/or may be noisy (e.g., as surfaces rub against one another), which may cause interference with some procedures (e.g., CT imaging). Other drawbacks of slip-ring assemblies may include cost and complexity of manufacture due to special materials and/or mechanical precision that may be required.

More recently, contactless assemblies have been devised to transfer the data (e.g., or electrical signals corresponding to the data) between the rotor and the stator. While such assemblies overcome many of the aforementioned drawbacks to a slip-ring assembly, the amount of data capable of being transferred via the foregoing contactless assemblies is limited. As radiation imaging modalities continue to develop (e.g., and transition to photon counting imaging modalities), data may be required to be transferred at much faster speeds. Further, data may be required to be transferred at a wider range of frequencies than either of the aforementioned assemblies is configured to handle.

BRIEF SUMMARY

Aspects of the present application address the above matters, and others. According to one aspect, a computed tomography (CT) imaging modality is provided. The CT imaging modality comprises a stator and a rotor configured to rotate relative to the stator. The CT imaging modality comprises a radiation source coupled to the rotor and configured to emit radiation. The CT imaging modality comprises a detector array coupled to the rotor and configured to detect at least some of the radiation. The CT imaging modality comprises a first data communication component coupled to the stator or the rotor for transmitting data between the stator and the rotor. The first data communication component comprises a first magnetic portion comprising a first magnetic material. The first data communication component comprises a first conductive portion comprising an electrically conductive material. The first conductive portion is at least partially surrounded by the first magnetic portion. The first magnetic portion and the first conductive portion form an electromagnetic coupling with a second data communication component. The second data communication component is coupled to the stator when the first data communication component is coupled to the rotor or the rotor when the first data communication component is coupled to the stator.

According to another aspect, a data communication system for wirelessly transmitting data is provided. The data communication system comprises a first magnetic portion comprising a first magnetic material. The first magnetic portion extends along a first axis. The data communication system comprises a first conductive portion comprising an electrically conductive material. The first conductive portion is at least partially surrounded by the first magnetic portion. The first conductive portion extends along a second axis that is substantially parallel to the first axis. The first conductive portion is configured to at least one of generate an electromagnetic field corresponding to data to be transmitted or have induced therein a current based upon a received electromagnetic field, the current a function of the data to be transmitted.

According to another embodiment, a data communication system for wirelessly transmitting data between a stator and a rotor is provided. The data communication system comprises a first data communication component coupled to the stator or the rotor for transmitting data between the stator and the rotor. The first data communication component comprises a first magnetic portion comprising a first magnetic material. The first data communication component comprises a first conductive portion comprising an electrically conductive material. The first conductive portion is at least partially surrounded by the first magnetic portion. The data communication system comprises a second data communication component coupled to the stator when the first data communication component is coupled to the rotor or the rotor when the first data communication component is coupled to the stator. The second data communication component comprises a second conductive portion comprising a second electrically conductive material. The second conductive portion is not surrounded by a magnetic portion comprising a magnetic material. The first magnetic portion and the first conductive portion form an electromagnetic coupling with the second data communication component.

Those of ordinary skill in the art will appreciate still other aspects of the present application upon reading and understanding the appended description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
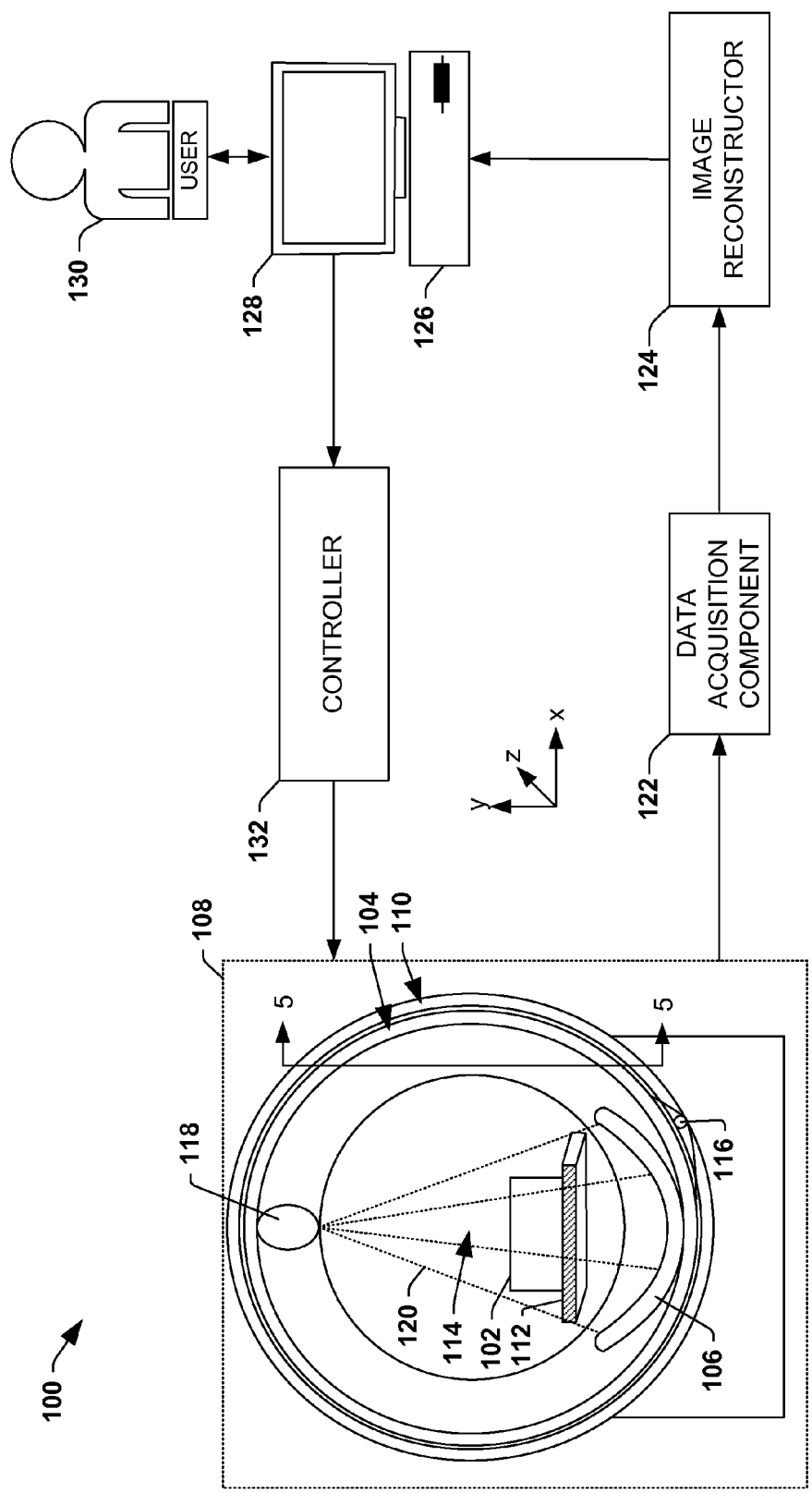
FIG. 1 is a schematic block diagram illustrating an example environment where a data communication system such as described herein may be implemented.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a data communication system for transferring data and/or information between two (or more) units. Typically, at least one of the units is movable (e.g., rotating) relative to the other unit. The two units may be separated by an airgap (or gap of some other medium, material, etc.). The data communication system can comprise two or more components. For example, the data communication system can comprise a first data communication component that can be coupled to a stator or a rotor. The data communication system can also comprise a second data communication component that can be coupled to the stator when the first data communication component is coupled to the rotor, or to the rotor when the first data communication component is coupled to the stator.

The first data communication component can transmit data to the second data communication component using electromagnetic coupling. For example, the first data communication component can generate an electromagnetic field that corresponds to data to be transmitted and an electromagnetic coupling is formed with the second data communication component. The second data communication component can have a current induced therein based upon the electromagnetic field generated by the first data communication component. A characteristic (e.g., frequency, amplitude, etc.) of the current may be indicative of a function of the data to be transmitted due to the electromagnetic field being a function of the data to be transmitted.

It may be appreciated that "noncontact," "contactless," and/or the like is used herein to refer to the ability to transmit information between or among bodies configured for relative movement, and should not be understood to necessarily preclude possible contact between or among such bodies for other purposes, comprising, for example, exchange or communication of data, mechanical drive or support, braking and safety mechanisms, etc.

It may also be appreciated that in the present disclosure, except where otherwise clear from context, "gap" and "airgap" are used more or less interchangeably; although "airgap" may be used herein, as this should be understood to be mere deference to convention, it should be understood that such gaps are not limited to air, it being possible for vacuum, oil, and/or other fluid and/or gas, and/or sliding and/or roller bearings or other such contrivances permitting relative movement to completely or partially fill such spaces. Further, "radiation imaging modality" and/or the like are intended to describe how the imaging modality utilizes radiation to perform an examination.

FIG. 1 is an illustration of an example environment 100 where a data communication system as provided for herein can be useful. More particularly, FIG. 1 illustrates an example computed tomography (CT) imaging modality that can be configured to transmit data regarding an object 102 under examination and generate images therefrom.

It may be appreciated that while a CT imaging modality is described herein, the instant application is not intended to be so limited. That is, to the extent practical, the instant application, including the scope of the claimed subject matter, is intended to be applicable to other apparatuses where an antenna and/or a data communication system comprising such an antenna can be useful. More particularly, the instant application is applicable to other apparatuses where supplying communication information (e.g., control information, status information, imaging information, etc.) to and/or from a movable unit of an apparatus would be useful. Moreover, the example environment 100 merely illustrates an example diagram and is not intended to be interpreted in a limiting manner, such as necessarily specifying the location, inclusion, and/or relative arrangement of the components described herein. For example, a data acquisition component 122 as illustrated in FIG. 1 can be part of a rotor 104 portion of an object examination apparatus 108, or more particularly can be part of a detector array 106, for example.

In the example environment 100, the object examination apparatus 108 is configured to examine one or more objects 102 (e.g., a series of suitcases at an airport, a human patient, etc.). The object examination apparatus 108 can comprise a rotor 104 and a stator 110. During an examination of the object(s) 102, the object(s) 102 can be placed on a support article 112, such as a bed or conveyor belt, that is selectively positioned in an examination region 114 (e.g., a hollow bore in the rotor 104 in which the object(s) 102 is exposed to radiation), and the rotor 104 can be rotated about the object(s) 102 by a rotator 116 (e.g., motor, drive shaft, chain, etc.).

The rotor 104 can surround a portion of the examination region 114 and can comprise one or more radiation sources 118 (e.g., an ionizing x-ray source, gamma-ray source, etc.) and a detector array 106 that is mounted on a substantially diametrically opposite side of the rotor 104 relative to the radiation source(s) 118. During an examination of the object(s) 102, the radiation source(s) 118 emits fan and/or cone shaped radiation 120 configurations into the examination region 114 of the object examination apparatus 108. It may be appreciated that such radiation 120 can be emitted substantially continuously and/or can be emitted intermittently (e.g., a short pulse of radiation 120 is emitted followed by a resting period during which the radiation source(s) 118 is not activated).

As the emitted radiation 120 traverses the object(s) 102, the radiation 120 can be attenuated differently by different aspects of the object(s) 102. Because different aspects attenuate different percentages of the radiation 120, an image(s) can be generated based upon the attenuation, or variations in the number of radiation photons that are detected by the detector array 106. For example, more dense aspects of the object(s) 102, such as a bone or metal plate, can attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using a scintillator and photodetectors and/or other indirect conversion materials) detected radiation into analog signals that can be transmitted from the detector array 106 to a data acquisition component 122 configured to convert the analog signals output by the detector array 106 into digital signals and/or to compile signals that were transmitted within a predetermined time interval, or measurement interval, using various techniques (e.g., integration, photon counting, etc.). It can be appreciated that such a measurement interval can be referred to as a "view" and generally reflects signals generated from radiation 120 that was emitted while the radiation source(s) 118 was at a particular angular range relative to the object 102. Based upon the compiled signals, the data acquisition component 122 can generate projection data indicative of the compiled signals, for example.

Information can be transmitted between components physically attached to the rotor 104 (e.g., such as the detector array 106 and/or data acquisition component 122) and components that are not physically attached to the rotor 104 (e.g., such as an image reconstructor 124) through a data communication system. By way of example, the projection space data (at times referred to as imaging data because it is used to reconstruct images of the object) generated by the data acquisition component 122 can be transmitted via the data communication system to an image reconstructor 124 positioned on the stator 110 of the imaging modality. As can be described in more detail below, such a data communication system typically comprises one or more data communication components mounted to the rotor 104 and to the stator 110, where an airgap generally separates a data communication component mounted to the rotor 104 from a data communication component mounted to the stator 110.

The image reconstructor 124 is configured to receive the projection space data that is output by the data acquisition component 122 and to generate image space data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also comprises a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed of a conveyor belt, activation of the radiation source(s) 118, etc.).

In the example environment 100, a controller 132 is operably coupled to the terminal 126. In one example, the controller 132 is configured to receive input from the terminal 126, such as user input, for example, and to generate instructions for the object examination apparatus 108 indicative of operations to be performed. For example, the user 130 can desire to reexamine the object(s) 102 at a different energy level, and the controller 132 can issue a command instructing the support article 112 to reverse direction (e.g., bringing the object(s) 102 back into an examination region 114 of the object examination apparatus 108) and instructing a power supply mounted to the rotor 104 to increase a voltage applied to the radiation source(s) 118 (e.g., causing the radiation 120 output therefrom to have a higher energy).

Figure 2A:
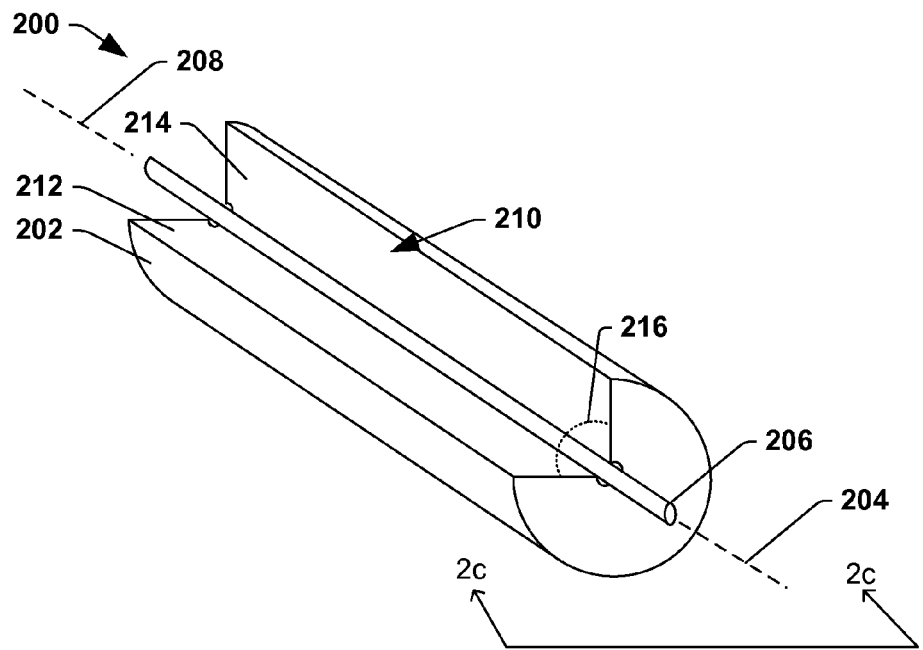
FIG. 2A illustrates a perspective view of an example first data communication component.
Figure 2B:
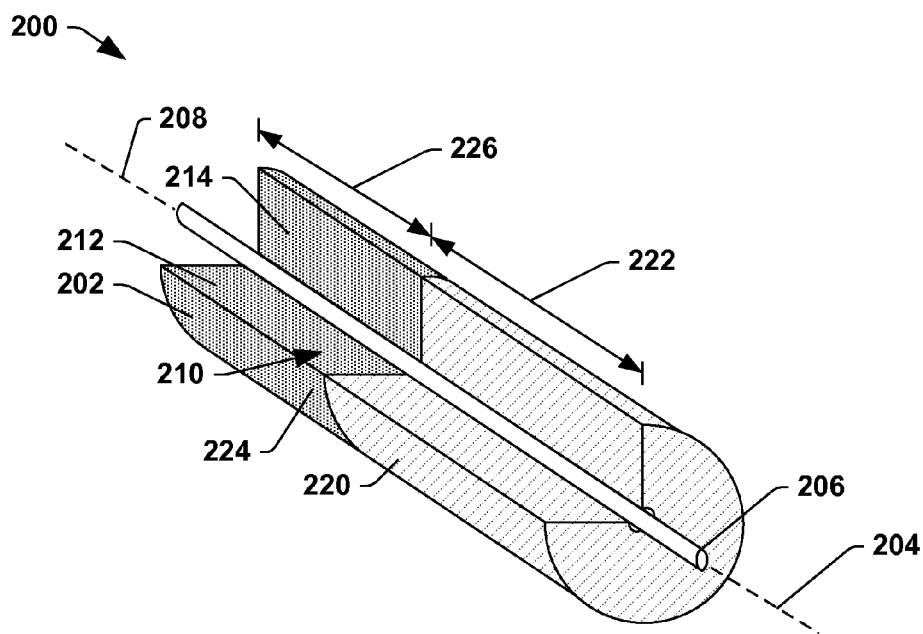
FIG. 2B illustrates an example first data communication component in which a first magnetic portion comprises a first magnetic material and a second magnetic material.
Figure 2C:
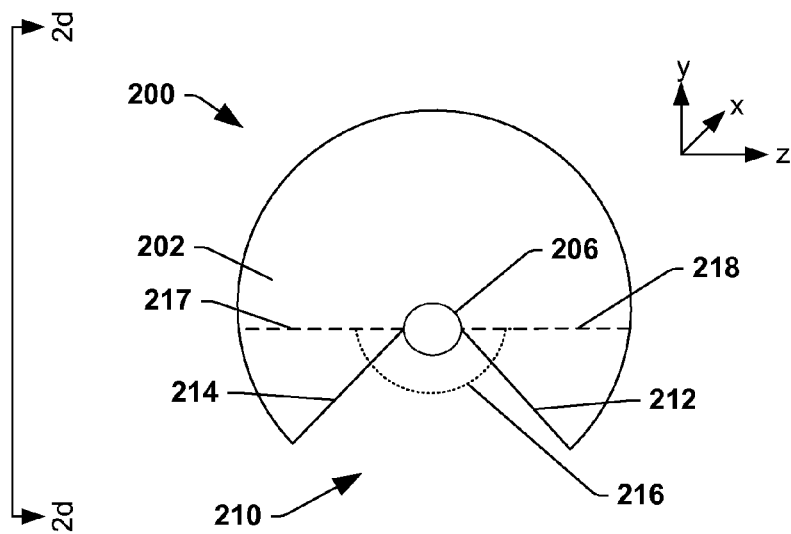
FIG. 2C illustrates an example first data communication component.
Figure 2D:
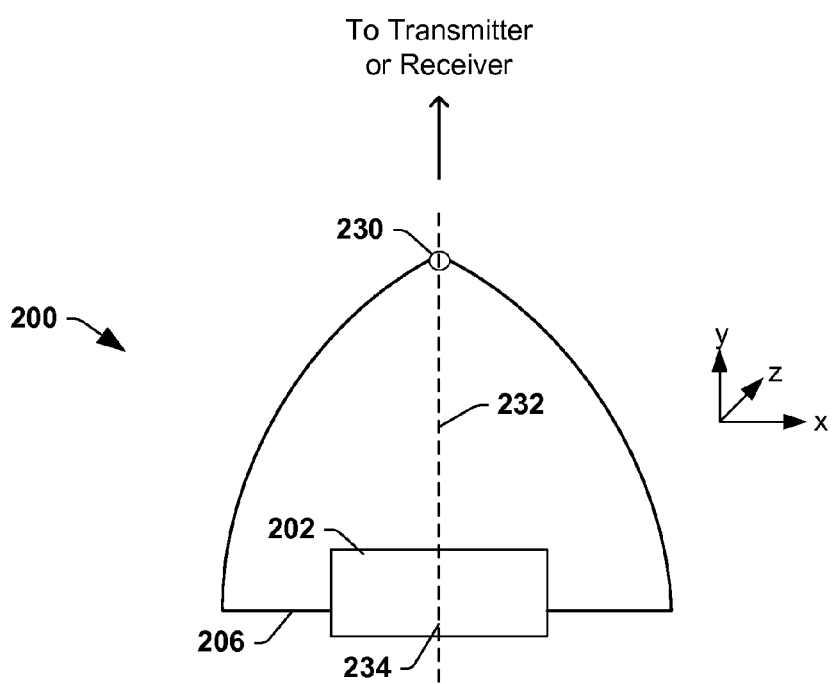
FIG. 2D illustrates an example first data communication component coupled to a first terminal.
Figure 3:
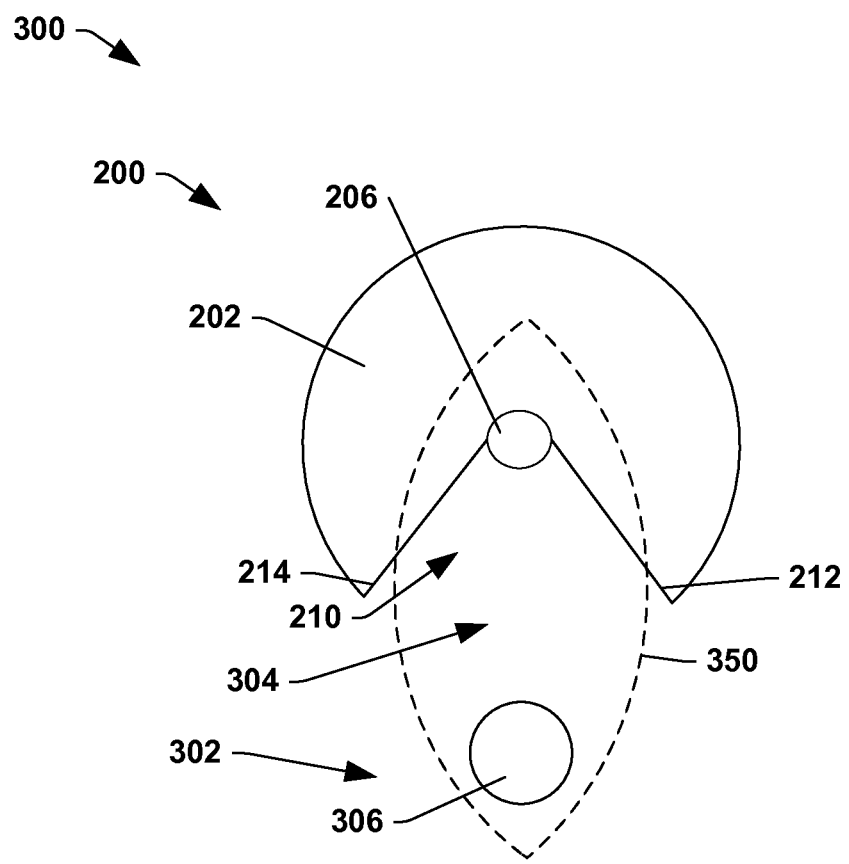
FIG. 3 illustrates an example data communication system.

FIGS. 2A, 2B, 2C and 2D illustrate an example first data communication component 200, which can be part of a data communication system 300 (e.g., illustrated in FIG. 3). In operation, the first data communication component 200 can be coupled to the stator 110 or the rotor 104 for wirelessly transmitting data between the stator 110 and the rotor 104. This data can comprise, for example, control information transmitted from the stator 110 to the rotor 104, imaging data transmitted from the rotor 104 to the stator 110, status information transmitted from the rotor 104 to the stator 110, etc.

The first data communication component 200 comprises a first magnetic portion 202 and a first conductive portion 206. The first magnetic portion 202 can comprise a first magnetic material. According to some examples, the first magnetic material is electrically non-conductive and magnetically permeable. The first magnetic material can comprise, for example, a ferrite material or other material that is substantially dielectric (e.g., electrically non-conductive) so that electric currents in the first magnetic portion 202 are mitigated. In general, the first magnetic portion 202 can generate a dipole field and will radiate strongly to a surrounding space, thus creating magnetic field flux loops. The first magnetic material of the first magnetic portion 202 can generally channel magnetic flux loops. The magnetic flux loops can extend beyond the region of the first magnetic portion 202 (e.g., escaping outwardly from the first magnetic portion 202) and induce electric currents in electrically conductive materials (e.g., wires, conductive strips, etc.) that are proximate the first magnetic portion 202, such as electrically conductive materials of the first conductive portion 206. The first magnetic portion 202 can extend along a first axis 204. In some examples, the first axis 204 has at least some degree of curvature and/or bend, as the first magnetic portion 202 can have a similar and/or matching shape as the stator 110 and/or the rotor 104, which are sometimes cylindrically shaped.

The first conductive portion 206 comprises an electrically conductive material. For example, the first conductive portion 206 can comprise a wire, electrical band, etc. The first conductive portion 206 comprises any number of materials, comprising copper, aluminum, and/or the like. In the illustrated example, the first conductive portion 206 can extend along a second axis 208. The second axis 208 can be substantially parallel to the first axis 204. In the illustrated example, the second axis 208 is collinear with the first axis 204. In some examples, the second axis 208 can have at least some degree of curvature and/or bend, as the first conductive portion 206 can have a similar and/or matching shape as the circular stator 110 or the circular rotor 104.

The first magnetic portion 202 can define a radial opening 210. In some embodiments, the radial opening 210 extends along a length of the first data communication component 200. In the illustrated example, the radial opening 210 extends along an entire length of the first data communication component 200 (e.g., where length corresponds to a direction in which the first axis 204 extends). In some embodiments, the radial opening 210 extends from a center of the first magnetic portion 202 radially outwardly towards an outer wall/surface of the first magnetic portion 202. The radial opening 210 is defined between a first wall 212 of the first magnetic portion 202 and a second wall 214 of the first magnetic portion 202.

An angle 216 can be defined between the first wall 212 and the second wall 214. In some examples, the angle 216 is between about 45 degrees to about 90 degrees. However, such a range is not intended to be limiting. Rather, in another example, the angle 216 can be greater than 90 degrees, such as by being between about 90 degrees to about 180 degrees. For example, referring briefly to FIG. 2C, a second position of a first wall 217 (illustrated with dashed lines) can define the angle 216 with respect to a second position of a second wall 218 (illustrated with dashed lines). In such an example, the angle 216 (e.g., defined between the first wall 217 and the second wall 218) can be about 180 degrees, though a wider range, such as about 135 degrees to about 225 degrees, is envisioned.

In some embodiments, the first magnetic portion 202 has a non-uniform material composition. For example, a first portion of the first magnetic portion 202 comprises a first magnetic material not included in a second portion of the first magnetic portion 202. Turning to FIG. 2B, an example configuration of the first magnetic portion 202 is illustrated, wherein the first magnetic portion 202 has a non-uniform material composition. In the illustrated example, the first magnetic portion 202 comprises a first magnetic material 220 that extends along a first length 222 of the first data communication component 200 and a second magnetic material 224, different than the first magnetic material 220, that extends along a second length 226 (e.g., which may or may not overlap the first length 222). For example, the first magnetic material 220 can comprise a first composition of ferrite and the second magnetic material 224 can comprise a second composition of ferrite that is different than the first composition.

In some examples, the first magnetic material 220 and the second magnetic material 224 can be in contact while in other examples, the first magnetic material 220 and the second magnetic material 224 can be separated by a gap, space, aperture, or the like. The first magnetic material 220 and the second magnetic material 224 can have different properties and, thus, can generate electromagnetic fields for communication of data of different frequencies. In an example, data pertaining to control information can be transmitted at a frequency of about 1 Megahertz (MHz) while data pertaining to imaging data can be transmitted at a frequency of about 4 MHz. In such an example, the first magnetic material 220 and the second magnetic material 224 can be provided to accommodate for these differing frequencies.

FIG. 2D illustrates a side view (e.g., as viewed from a perspective along line 2d-2d in FIG. 2C) of the first data communication component 200. In this example, the first conductive portion 206 terminates at a first terminal 230. The first terminal 230 can comprise an electrical component, point of connection, or the like at which ends of the first conductive portion 206 are electrically connected. In some examples, the first terminal 230 can be electrically connected to a transmitter or a receiver.

In the illustrated example, the first magnetic portion 202 is aligned and/or centered with respect to the first terminal 230. That is, the first terminal 230 can be positioned proximate a center portion 234 of the first magnetic portion 202. By being positioned proximate the center portion 234, a terminal axis 232 of the first terminal 230 (e.g., an imaginary line drawn from the first terminal 230 and intersecting the first magnetic portion 202 at a perpendicular angle) can extend through (e.g., intersect) the center portion 234 of the first magnetic portion 202. As such, the first data communication component 200 can receive data from a second data communication component 302 (illustrated in FIG. 3) regardless of the direction of current through the second data communication component 302 (e.g., regardless of whether the current is moving left-to-right on the page or right-to-left on the page), for example.

Turning to FIG. 3, an example of the data communication system 300 for wirelessly transmitting data is illustrated. The data communication system 300 comprises two data communication components, such as the first data communication component 200 and the second data communication component 302. In an example, the second data communication component 302 can be coupled to the stator 110 when the first data communication component 200 is coupled to the rotor 104. In another example, the second data communication component 302 can be coupled to the rotor 104 when the first data communication component 200 is coupled to the stator 110.

The first data communication component 200 can be separated from the second data communication component 302 by an airgap 304. The airgap 304 defines a space, channel, opening, etc. that enables rotation of the rotor 104 with respect to the stator 110. In general, the first data communication component 200 can be mounted within and/or adjacent a first side of the airgap 304. The second data communication component 302 can be mounted within and/or adjacent a second side of the airgap 304 that is opposite the first side. A distance between the first data communication component 200 and the second data communication component 302 can be relatively small, such as less than about 20 mm, although the distance can be larger than 20 mm (e.g., such as up to a few inches).

The second data communication component 302 can comprise a second conductive portion 306. The second conductive portion 306 comprises an electrically conductive material. For example, the second conductive portion 306 can comprise a wire, band, etc. The second conductive portion 306 comprises any number of materials, comprising copper, aluminum, and/or the like. In the illustrated example, the second conductive portion 306 can extend along an axis that is substantially parallel to the first axis 204 and/or to the second axis 208. In some examples, the second conductive portion 306 can have at least some degree of curvature and/or bend, as the second conductive portion 306 can have a similar and/or matching shape as the stator 110 or the rotor 104. In the illustrated example, the second conductive portion 306 is not surrounded by a magnetic portion (e.g., unlike the first conductive portion 206).

The first magnetic portion 202 and the first conductive portion 206 can form an electromagnetic coupling 350 with the second data communication component 302. In an example, to form the electromagnetic coupling 350, the first conductive portion 206 can generate an electromagnetic field that corresponds to data to be transmitted and an electromagnetic coupling 350 can be formed with the second data communication component 302. The second data communication component 302 can have a current induced therein based upon the received electromagnetic field from the first data communication component 200. A characteristic (e.g., frequency, amplitude, etc.) of the current can be indicative of the data (e.g., control information, imaging data, status information, etc.) to be transmitted.

In another example, the first conductive portion 206 can have induced therein a current based upon a received electromagnetic field from the second data communication component 302. For example, the second data communication component 302 can generate an electromagnetic field that corresponds to data to be transmitted. The second data communication component 302 can form the electromagnetic coupling 350 with the first data communication component 200. In such an example, a current induced in the first conductive portion 206 can be a function of the data to be transmitted from the second data communication component 302 to the first data communication component 200. In the aforementioned examples, the first conductive portion 206 can be exposed to the second data communication component 302 through the radial opening 210.

Figure 4A:
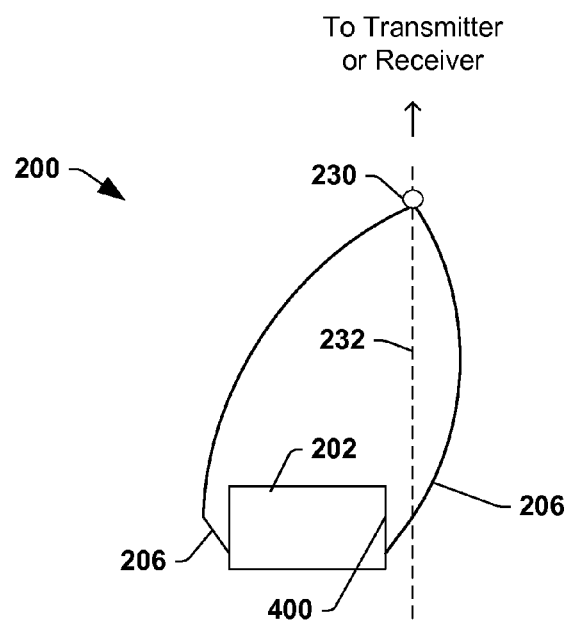
FIG. 4A illustrates an example first data communication component.

Turning to FIG. 4A, an example configuration of the first data communication component 200 is illustrated. The first data communication component 200 is similar in some respects to the first data communication component 200 described above with respect to FIGS. 2-3. For example, the first data communication component 200 can comprise the first magnetic portion 202, the first conductive portion 206, etc. In the illustrated example, the first magnetic portion 202 comprises a single magnetic material, although in other embodiments, the first magnetic portion 202 can comprise a plurality of magnetic materials.

The first conductive portion 206 can terminate at the first terminal 230. In the illustrated example, the first terminal 230 can be positioned proximate a first distal end 400 of the first magnetic portion 202. The first terminal 230 defines the terminal axis 232 that extends from the first terminal 230. In this example, the first magnetic portion 202 can be misaligned and/or off-centered with respect to the first terminal 230. That is, the terminal axis 232 of the first terminal 230 may not intersect and/or extend through the first magnetic portion 202. Instead, the terminal axis 232, and, thus, the first terminal 230, can be positioned proximate the first distal end 400 of the first magnetic portion 202.

Figure 4B:
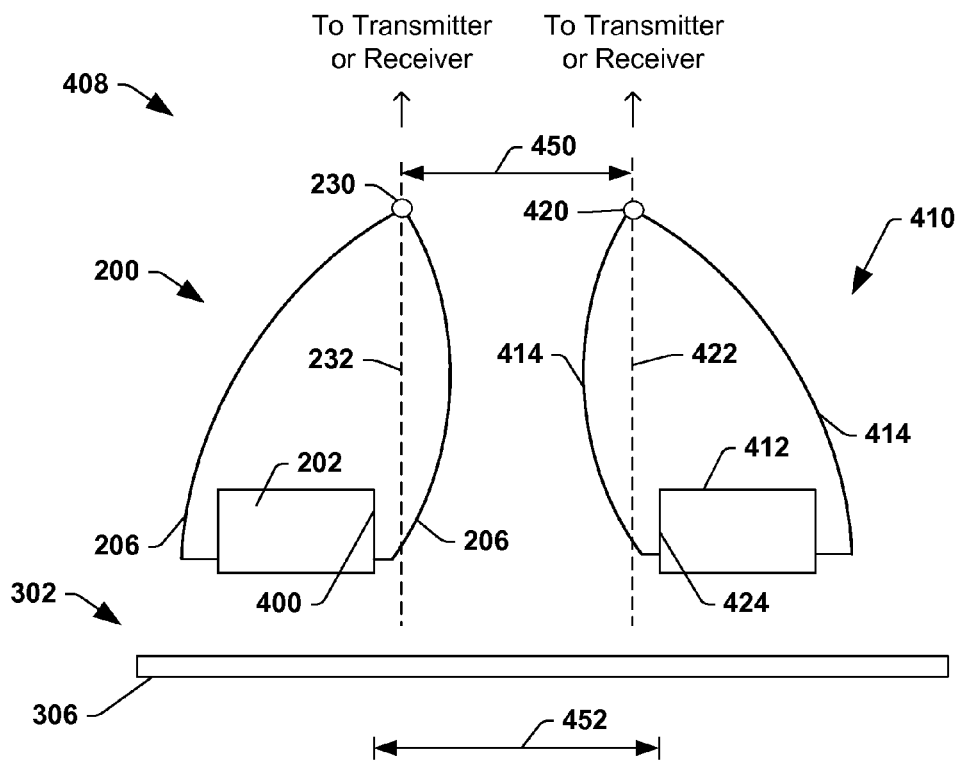
FIG. 4B illustrates a second example data communication system.

Turning to FIG. 4b, another example data communication system 408 for wirelessly transmitting data is illustrated. The data communication system 408 comprises the first data communication component 200 and the second data communication component 302, which comprises the second conductive portion 306. The first data communication component 200 is generally similar in structure and/or function to the first data communication component of FIG. 4a, and can comprise the first magnetic portion 202, the first conductive portion 206, etc. In this example, the first terminal 230 can be positioned proximate the first distal end 400 of the first magnetic portion 202.

The data communication system 408 can also comprise a third data communication component 410. According to some examples, the third data communication component 410 is generally similar in structure to the first data communication component 200. For example, the third data communication component 410 can be coupled to the stator 110 or the rotor 104 for transmitting data between the stator 110 and the rotor 104. The third data communication component 410 can be coupled to the same structure (e.g., stator 110 or the rotor 104) as the first data communication component 200. For example, the third data communication component 410 can be coupled to the stator 110 when the first data communication component 200 is coupled to the stator 110. Likewise, the third data communication component 410 can be coupled to the rotor 104 when the first data communication component 200 is coupled to the rotor 104. In either of these examples, the second data communication component 302 is not coupled to the same structure (e.g., stator 110 or the rotor 104) as the first data communication component 200 and the third data communication component 410.

The third data communication component 410 can comprise a third magnetic portion 412 that comprises a third magnetic material. The third magnetic portion 412 is generally similar in structure to the first magnetic portion 202 of the first data communication component 200, although the third magnetic material can be different than one or more magnetic materials of the first magnetic portion 202. For example, the third magnetic material can be electrically non-conductive and magnetically permeable. The third magnetic material can comprise, for example, a ferrite material or other material that is substantially dielectric (e.g., electrically non-conductive) so that electric currents in the third magnetic portion 412 are mitigated. In general, the third magnetic portion 412 can generate a dipole field and will radiate strongly to a surrounding space, thus creating magnetic field flux loops. The third magnetic portion 412 can comprise a radial opening similar in structure to the radial opening 210 illustrated in FIGS. 2a-2c.

The third data communication component 410 can comprise a third conductive portion 414. The third conductive portion 414 is generally similar in structure to the first conductive portion 206 of the first data communication component 200. The third conductive portion 414 comprises a third electrically conductive material. For example, the third conductive portion 414 can comprise a wire, band, etc. The third conductive portion 414 comprises any number of materials, comprising copper, aluminum, and/or the like. The third conductive portion 414 can be at least partially surrounded by the third magnetic portion 412, such that the third conductive portion 414 extends within and through the third magnetic portion 412. The third magnetic portion 412 and the third conductive portion 414 can form an electromagnetic coupling (similar in function to the electromagnetic coupling 350 illustrated in FIG. 3) with the second data communication component 302.

The third conductive portion 414 can terminate at a third terminal 420. The third terminal 420 is generally similar in structure and function to the first terminal 230. In the illustrated example, the third terminal 420 can be positioned proximate a second distal end 424 of the third magnetic portion 412. The third terminal 402 defines a third terminal axis 422 extending from the third terminal 402 and intersecting the third conductive portion 414 at a perpendicular angle (or intersecting the third conductive portion 414 at a perpendicular angle if the third conductive portion 414 was extended to intersect the third terminal axis 422).

In this example, the third magnetic portion 412 can be misaligned and/or off-centered with respect to the third terminal 420. That is, the third terminal axis 422 of the third terminal 420 may not intersect and/or extend through the third magnetic portion 412. Instead, the third terminal axis 422, and, thus, the third terminal 420, can be positioned proximate the second distal end 424 of the third magnetic portion 412.

The first distal end 400 of the first magnetic portion 202 can be adjacent the second distal end 424 of the third magnetic portion 412. For example, a first separating distance 450 is a distance that separates the first terminal 230 (e.g., the terminal axis 232) from the third terminal 420 (e.g., the third terminal axis 422). A second separating distance 452 is a distance that separates the first distal end 400 of the first magnetic portion 202 from the second distal end 424 of the third magnetic portion 412. In the illustrated example, the first separating distance 450 separating the first terminal 230 from the third terminal 420 is less than the second separating distance 452 separating the first magnetic portion 202 from the third magnetic portion 412. In other embodiments, the first separating distance 450 can be greater than the second separating distance 452.

Accordingly, the first data communication component 200 and the third data communication component 410 are off-centered with respect to the first terminal 230 and the third terminal 420, respectively. By being offcentered, the first data communication component 200 and the third data communication component 410 can receive a current flowing through the second data communication component 302 left-to-right on the page (e.g., which would be detected by the first data communication component 200) or right-to-left on the page (e.g., which would be detected by the third data communication component 410).

Figure 5:
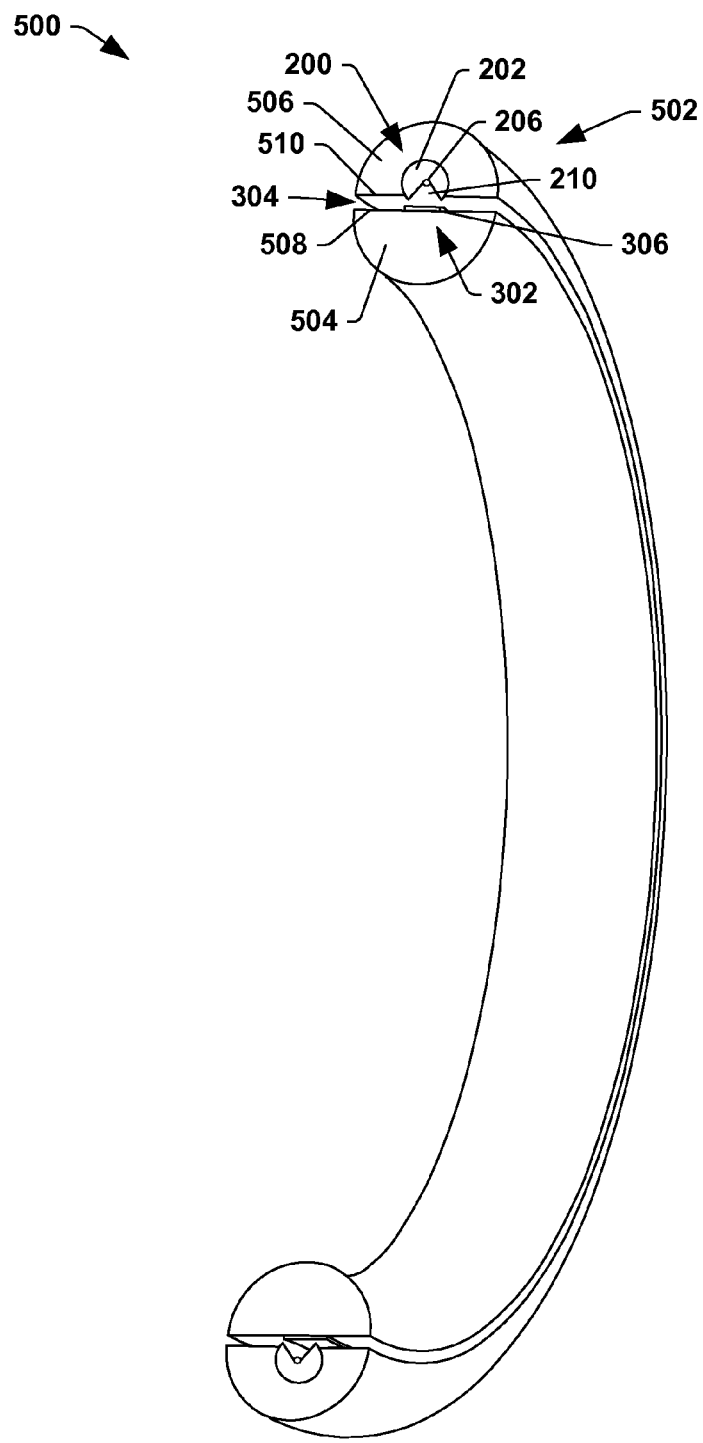
FIG. 5 illustrates an example rotor and stator, with a data communication system coupled to the rotor and the stator.

FIG. 5 illustrates a cross-sectional view 500 (e.g., taken along line 5-5 in FIG. 1) of a data communication system 502 that is mounted to a radial surface of a rotor 504 (e.g., 104 in FIG. 1) and/or a stator 506 (e.g., 110 in FIG. 1). As illustrated herein, the rotor 504 and the stator 506 are respectively half circles separated from one another via the airgap 304 which enables rotation of the rotor 504 relative to the stator 506. As described herein, data is configured to be wirelessly transmitted between the rotor 504 and the stator 506. In this way, data can be supplied to and/or from components comprised within the rotor 504, such as the radiation source(s) 118, the detector array 106, etc.

The second data communication component 302, which can comprise the second conductive portion 306, can be coupled to an exterior radial surface 508 of the rotor 504. In another embodiment, the second data communication component 302 can be coupled to an interior radial surface 510 of the stator 506. In the illustrated example, the second data communication component 302 (e.g., the second conductive portion 306) can extend substantially continuously around the entire exterior radial surface 508 of the rotor 504 or around the entire interior radial surface 510 of the stator 506. As such, the second data communication component 302 can form a nearly complete ring.

The first data communication component 200 (and the third data communication component 410, illustrated in FIG. 4b) can be coupled to the interior radial surface 510 of the stator 506 when the second data communication component 302 is coupled to the exterior radial surface 508 of the rotor 504. In an alternative example, the first data communication component 200 (and the third data communication component 410, illustrated in FIG. 4b) can be coupled to the exterior radial surface 508 of the rotor 504 when the second data communication component 302 is coupled to the interior radial surface 510 of the stator 506. In these examples, the radial opening 210 defined within the first magnetic portion 202 can face the second conductive portion 306 of the second data communication component 302. As such, the first conductive portion 206 is exposed to the second data communication component 302 through the radial opening 210.

In some examples, the first data communication component 200 (and the third data communication component 410) may not extend along the entire surface of the rotor 504 and/or the stator 506. Indeed, the first data communication component 200 (and the third data communication component 410) can be coupled to merely a small portion of the rotor 504 and/or the stator 506. In this way, as the rotor 504, comprising the second data communication component 302, rotates, a portion of the second data communication component 302 remains in close spatial proximity to the first data communication component 200 (and the third data communication component 410) allowing for data communication between the rotor 504 and the stator 506.

Figure 6:
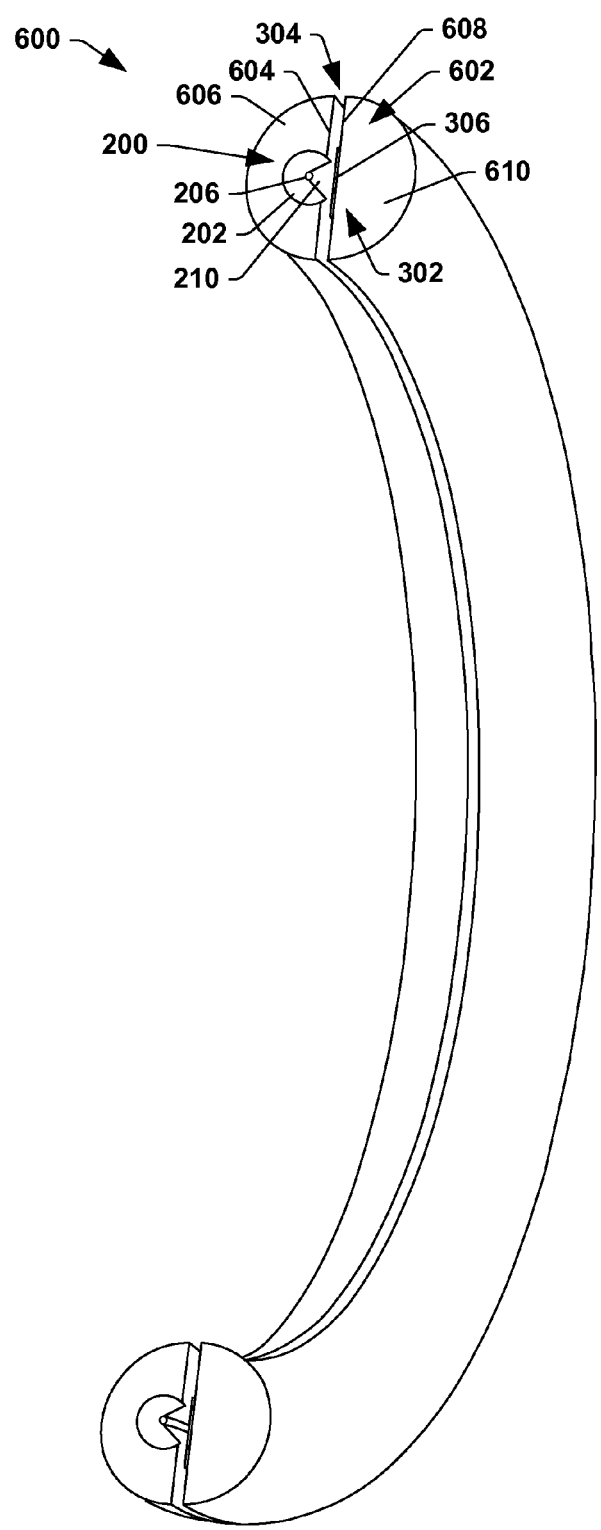
FIG. 6 illustrates an example rotor and stator, with a data communication system coupled to the rotor and the stator.

FIG. 6 illustrates a cross-sectional view 600 of another embodiment for mounting a data communication system 602 to a movable unit and/or a stator. More particularly, FIG. 6 illustrates the first data communication component 200 mounted to an axial surface 604 of a rotor 606. The second data communication component 302 can be mounted to an axial surface 608 of a stator 610.

As described with respect to FIG. 5, at least one of the first data communication component 200 and the second data communication component 302 can extend along substantially an entire surface of the rotor 606 and/or the stator 610 (e.g., forming a nearly complete ring). For example, in the illustrated embodiment, the second data communication component 302 follows the circumference of the stator 610, while the first data communication component 200 is mounted to merely a small portion of the axial surface 604 of the rotor 606. As such, as the rotor 606, comprising the first data communication component 200, rotates, a portion of the second data communication component 302 remains in close spatial proximity to the first data communication component 200. Accordingly, the first magnetic portion 202 and the first conductive portion 206 form an electromagnetic coupling with the second data communication component 302.

It may be appreciated that various advantages may arise based on the use of the data communication system 300. For example, wireless communication of data between a rotor and a stator can be provided with the data communication components described herein. For example, data pertaining to control information can be wirelessly transmitted between the rotor and the stator for instructing the radiation source and/or other electronic components how to operate. Likewise, data pertaining to imaging data can be wirelessly transmitted between the rotor and the stator, with the imaging data generated in response to the detection of radiation by the detector array. In these examples, electromagnetic coupling between the communication components can allow for a larger amount of data to be transferred and for faster transfer speeds.

In an example, a method of wirelessly transmitting data with the data communication system can be provided. The method comprises receiving transmission data to be transmitted between a rotor 104 and a stator 110. The method comprises translating the transmission data into an analog signal (e.g., AC signal). The method comprises applying the analog signal to a first conductive portion (e.g., the first conductive portion 206) to create an electromagnetic field. The method comprises inducing a current in a second conductive portion (e.g., the second conductive portion 306) based upon the electromagnetic field to generate an induced current. The method comprises translating the induced current into received data. In an example, the induced current is a function of a magnetic B-field. In an example, the received data can substantially match the transmission data.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A computed tomography (CT) imaging modality comprising:
   a stator;
   a rotor configured to rotate relative to the stator;
   a radiation source coupled to the rotor and configured to emit radiation;
   a detector array coupled to the rotor and configured to detect at least some of the radiation; and
   a first data communication component coupled to the stator or the rotor for transmitting data between the stator and the rotor, the first data communication component comprising:
      a first magnetic portion comprising a first magnetic material; and
      a first conductive portion comprising an electrically conductive material, the first conductive portion at least partially surrounded by the first magnetic portion, the first magnetic portion and the first conductive portion forming an electromagnetic coupling with a second data communication component, the second data communication component coupled to:
         the stator when the first data communication component is coupled to the rotor; or
         the rotor when the first data communication component is coupled to the stator.

2. The CT imaging modality of claim 1, wherein the second data communication component comprises a second conductive portion comprising a second electrically conductive material, the second conductive portion not surrounded by a magnetic portion comprising a magnetic material.

3. The CT imaging modality of claim 1, wherein the first conductive portion terminates at a first terminal, the first terminal positioned proximate a first distal end of the first magnetic portion.

4. The CT imaging modality of claim 3, comprising:
   a third data communication component coupled to the stator or the rotor for transmitting data between the stator and the rotor, the third data communication component comprising:
      a third magnetic portion comprising a third magnetic material; and
      a third conductive portion comprising a third electrically conductive material, the third conductive portion at least partially surrounded by the third magnetic portion, the third magnetic portion and the third conductive portion forming an electromagnetic coupling with the second data communication component;

wherein the third conductive portion terminates at a third terminal, the third terminal positioned proximate a second distal end of the third magnetic portion, the first distal end of the first magnetic portion adjacent the second distal end of the third magnetic portion.

5. The CT imaging modality of claim 1, wherein the first conductive portion terminates at a first terminal, the first terminal positioned proximate a center portion of the first magnetic portion.

6. The CT imaging modality of claim 1, wherein the first magnetic portion defines a radial opening extending along a length of the first data communication component.

7. The CT imaging modality of claim 6, wherein the first conductive portion is exposed to the second data communication component through the radial opening.

8. The CT imaging modality of claim 1, wherein the first magnetic material is electrically non-conductive and magnetically permeable, the first magnetic portion comprising a second magnetic material that is electrically non-conductive and magnetically permeable, the second magnetic material different than the first magnetic material.

9. The CT imaging modality of claim 8, wherein the first magnetic material extends along a first length of the first data communication component and the second magnetic material extends along a second length of the first data communication component that does not overlap the first length.

10. The CT imaging modality of claim 1, wherein the first data communication component is configured to transmit data to the second data communication component using the electromagnetic coupling.

11. The CT imaging modality of claim 10, wherein the second data communication component is configured to transmit data to the first data communication component using the electromagnetic coupling.

12. The CT imaging modality of claim 1, wherein the second data communication component is configured to transmit data to the first data communication component using the electromagnetic coupling.

13. The CT imaging modality of claim 1, wherein the first conductive portion is configured to have induced therein a current based upon a received electromagnetic field from the second data communication component, the current a function of the data to be transmitted.

14. A data communication system for wirelessly transmitting data, the data communication system comprising:
 a first magnetic portion comprising a first magnetic material, the first magnetic portion extending along a first axis; and
 a first conductive portion comprising an electrically conductive material, the first conductive portion at least partially surrounded by the first magnetic portion, the first conductive portion extending along a second axis that is substantially parallel to the first axis, the first conductive portion configured to at least one of:
  generate an electromagnetic field corresponding to data to be transmitted; or
  have induced therein a current based upon a received electromagnetic field, the current a function of the data to be transmitted.

15. The data communication system of claim 14, wherein the first magnetic material is electrically non-conductive and magnetically permeable.

16. The data communication system of claim 15, wherein the first magnetic portion comprises a second magnetic material that is electrically non-conductive and magnetically permeable, the second magnetic material different than the first magnetic material.

17. A data communication system for wirelessly transmitting data between a stator and a rotor, the data communication system comprising:
 a first data communication component coupled to the stator or the rotor for transmitting data between the stator and the rotor, the first data communication component comprising:
  a first magnetic portion comprising a first magnetic material; and
  a first conductive portion comprising an electrically conductive material, the first conductive portion at least partially surrounded by the first magnetic portion; and
 a second data communication component coupled to:
  the stator when the first data communication component is coupled to the rotor; or
  the rotor when the first data communication component is coupled to the stator;
 the second data communication component comprising:
  a second conductive portion comprising a second electrically conductive material, the second conductive portion not surrounded by a magnetic portion comprising a magnetic material, the first magnetic portion and the first conductive portion forming an electromagnetic coupling with the second data communication component.

18. The data communication system of claim 17, wherein the first conductive portion terminates at a first terminal, the first terminal positioned proximate a first distal end of the first magnetic portion.

19. The data communication system of claim 18, comprising:
 a third data communication component coupled to the stator or the rotor for transmitting data between the stator and the rotor, the third data communication component comprising:
  a third magnetic portion comprising a third magnetic material; and
  a third conductive portion comprising a third electrically conductive material, the third conductive portion at least partially surrounded by the third magnetic portion, the third magnetic portion and the third conductive portion forming an electromagnetic coupling with the second data communication component;
 wherein the third conductive portion terminates at a third terminal, the third terminal positioned proximate a second distal end of the third magnetic portion, the first distal end of the first magnetic portion adjacent the second distal end of the third magnetic portion.

20. The data communication system of claim 17, wherein the first conductive portion terminates at a first terminal, the first terminal positioned proximate a center portion of the first magnetic portion.

\* \* \* \* \*